United States Patent [19]

Boguslawski et al.

[11] 4,355,103

[45] Oct. 19, 1982

[54] NOVEL STRAIN OF *BACILLUS LICHENIFORMIS* USEFUL IN THE PRODUCTION OF GLUCOSE ISOMERASE AND METHOD OF SCREENING BACILLUS MUTANTS FOR ABILITY TO PRODUCE GLUCOSE ISOMERASE IN THE ABSENCE OF XYLOSE

[75] Inventors: George Boguslawski; Michael J. Rynski, both of Elkhart, Ind.

[73] Assignee: Miles Laboratories, Inc., Elkhart, Ind.

[21] Appl. No.: 227,686

[22] Filed: Jan. 23, 1981

[51] Int. Cl.³ .................. C12Q 1/04; C12N 15/00; C12N 9/92; C12N 1/20

[52] U.S. Cl. .................................. 435/34; 435/94; 435/172; 435/234; 435/253

[58] Field of Search ................ 435/234, 172, 253, 94, 435/34

[56] References Cited

U.S. PATENT DOCUMENTS

| 3,826,714 | 7/1974 | Suekane et al. | 435/234 X |
| 3,979,261 | 9/1976 | Outtrup | 435/234 |
| 4,283,496 | 8/1981 | Lee | 435/253 |
| 4,310,628 | 1/1982 | Leiser | 435/94 |

*Primary Examiner*—Lionel M. Shapiro
*Attorney, Agent, or Firm*—Jerome L. Jeffers

[57] ABSTRACT

A novel strain of *Bacillus licheniformis*, ATCC 31667, capable of producing glucose isomerase in the absence of xylose is disclosed. Also disclosed is a novel method for screening Bacillus mutants for this property.

7 Claims, No Drawings

NOVEL STRAIN OF *BACILLUS LICHENIFORMIS* USEFUL IN THE PRODUCTION OF GLUCOSE ISOMERASE AND METHOD OF SCREENING BACILLUS MUTANTS FOR ABILITY TO PRODUCE GLUCOSE ISOMERASE IN THE ABSENCE OF XYLOSE

BACKGROUND OF THE INVENTION

Sweet syrups consisting of sucrose (cane sugar) or dextrose-containing products obtained from starch hydrolysis are widely used in the baking, confectionery and beverage industries. Syrups containing a mixture of glucose and fructose are also widely used in industry because of their sweet taste (sweeter than sucrose) and low tendency to crystallize. Such syrups are commonly produced from glucose syrups using a glucose isomerase to catalyze the isomerization of glucose to fructose. While glucose is somewhat less sweet than sucrose, fructose is considerably sweeter than sucrose so that the overall sweetness of the treated glucose syrup is greater than that of sucrose. Glucose isomerases can be obtained from a large number of species of microorganisms.

In a typical method for the production of glucose isomerase, the microorganisms are cultivated on media containing inorganic salts and sources of carbon and nitrogen at a pH between pH 5 and pH 9. Microorganisms suitable for use in this method have been extensively characterized as is described by Buck, in *Enzyme and Fermentation Biotechnology*, Halsted Press, London, Pp 147-171 (1977). The use of many of the microorganisms useful for the production of glucose isomerase requires the introduction of xylose or a xylose-containing compound to the growth medium in order to induce glucose isomerase formation. However, pure xylose is too expensive to be used in commercial fermentation processes thereby rendering desirable mutant strains which, when cultivated, are capable of metabolizing carbon sources other than xylose. The random screening of mutant strains of cells from the Bacillus genus is extremely burdensome since it is often necessary to screen thousands of mutants in order to obtain one having the desired properties.

Novo Industri A/S has disclosed the production of α-amylase from *Bacillus licheniformis* in Process Biochem., 10 (4), 17-19 (1975) and copending application Ser. No. 156,496, filed June 4, 1980 and commonly assigned herewith discloses the use of *Bacillus licheniformis* in the production of glucose isomerase.

SUMMARY OF THE INVENTION

The present invention is an asporogenic bacterium from the genus and species *Bacillus licheniformis* (ATCC 31667). This bacterium is resistant to 2-deoxyglucose and is capable of producing glucose isomerase in greater quantities in a fermentation medium containing appropriate nutrients but no xylose, than in a medium in which xylose is present. The nutritional demands of this strain include the requirement of methionine and the vitamins niacin, riboflavin and thiamine for growth. Also included within the scope of the present invention is a method of producing glucose isomerase using the novel bacterium and the glucose isomerase produced by such method. The novel strain of *Bacillus licheniformis* and mutants of other species from the Bacillus genus having the desirable property of producing glucose isomerase in a medium devoid of xylose are isolated by a method comprising the steps of (a) placing a culture of a nonpathogenic bacterium from the genus Bacillus on a growth support medium;

(b) allowing the culture to grow and isolating a single colony to obtain a pure clone;

(c) streaking a single colony of the pure clone on a growth support medium containing 2-deoxyglucose;

(d) recovering one or more 2-deoxyglucose resistant variants from the growth support medium used in step (c);

(e) purifying the 2-deoxyglucose resistant variant obtained in step (d) by restreaking it on a growth support medium containing 2-deoxyglucose to thereby eliminate non-resistant dormant cells;

(f) recovering the purified variant from the growth support medium used in step (e); and (g) determining the ability of the purified varient to produce glucose isomerase in a growth support medium devoid of xylose.

DESCRIPTION OF THE INVENTION

A typical solid medium for use in the screening method of this invention will comprise peptone, amino acids, nitrogen source, vitamins, a carbohydrate, potassium phosphate, magnesium sulfate, and agar.

The screening method provides the researcher with a convenient tool for isolating mutant strains of bacteria from the genus Bacillus which have the ability to produce glucose isomerase in a growth medium devoid of xylose. This is the case because it has been determined that the likelihood of a 2-deoxyglucose resistant mutant having this property is much greater than is the case with variants which are not resistant to 2-deoxyglucose. Therefore, the number of mutants which must be screened is dramatically reduced. The screening technique can be used with any species of the Bacillus genus which is capable of producing glucose isomerase. Nonpathogenic organisms are, of course, employed since the enzyme produced is used in food processing. Particular organisms which can be successfully screened by the method of this invention include *Bacillus licheniformis, B. coagulans, B. subtilis, B. pumilus* and *B. cereus*.

A preferred organism prepared by the process of the present invention is the result of the spontaneous mutation of *Bacillus licheniformis* ATCC 31604 when this strain is grown on a medium containing 2-deoxyglucose. This compound generally interferes with reactions of glucose metabolism (e.g., glycolysis), usually through conversion to phosphorylated form, 2-deoxyglucose-6-phosphate. The phosphorylated form cannot be further processed.

Mutations to 2-deoxyglucose resistance can fall in several categories, e.g., the cells may (1) become impermeable to the inhibitor, (2) lose the ability to phosphorylate 2-deoxyglucose, (3) become independent of glucose as a carbon source or (4) overproduce enzymes for utilization of alternative carbon sources. The property of resistance to 2-deoxyglucose provides a convenient means to isolate the mutant strain and is also an identifying characteristic of the strain.

The novel strain of *Bacillus licheniformis* which is claimed herein has been deposited with the American Type Culture Collection, Rockville, Maryland and has been given the identification number ATCC 31667. This culture is available to the public without restriction. The strain is further identified in that it produces more glucose isomerase in a fermentation medium devoid of xylose than in one containing xylose, it does not utilize xylose as a carbon source and is resistant to 2-deoxyglucose. The strain is further identified in that it is asporogenic and that it requires methionine and the vitamins niacin, riboflavin and thiamine for growth.

The *Bacillus licheniformis* ATCC 31667 organism is resistant to 2-deoxyglucose and, as with other Bacillus strains isolated by the process disclosed herein, it is this resistance the results in identification and isolation of the mutant strain. Once isolated, the mutant strain can be maintained on agar slants and can be grown in a medium containing appropriate nutrients. A preferred growth environment involves a medium containing 1% Ardamine PH yeast extract, 1% D-glucose, 0.5% NaCl combined with the necessary amount of distilled $H_2O$, a temperature of about 50° C. and a pH in the range of 7 to 8.

The desired glucose isomerase is formed inside the bacterial cells as they grow. As can be determined from Example II, supra, this growth can be carried out with the level of dissolved oxygen being maintained at or over 20% or allowed to drop to zero. In either case air is being pumped through the fermentor which is preferable to the type of fermentation in which dissolved oxygen must be held very low since aeration is the most economical means of agitating the fermentation medium. The cells can be separated from the fermentation beer by conventional means such as filtration or centrifugation and used directly as a source of glucose isomerase. The cells can be agglomerated and the enzyme activity immobilized therein by state-of-the-art techniques such as the glutaraldehyde treatment disclosed in U.S. Pat. No. 3,779,869. Alternatively, the cells can be ruptured either mechanically or by autolysis and the soluble enzyme separated from the cell debris. The soluble enzyme can then be used directly or it can be immobilized on a suitable carrier.

The present invention is further illustrated by the following examples where the designation q/s indicates "as needed" and all percentages on a weight/volume basis.

EXAMPLE I

A stock culture of *Bacillus licheniformis* ATCC 31604 was grown in a liquid medium consisting of:
Ardamine PH yeast extract: 1.0%
D-xylose: 1.0%
NaCl: 0.5%
Distilled $H_2O$: q/s at 50° C. and at an initial pH of 7.15. The cells were grown to a Klett density of about 60 (green filter), centrifuged and resuspended in 0.1 M $MgSO_4$ so that the optical density at 540 nm was 0.150 as determined by the use of a Bausch & Lomb Spectronic 20 spectrophotometer. A loopful of this suspension was streaked on a solid medium containing a gradient of 2-deoxy-D-glucose concentration from 0 to 3%. The composition of the solid medium was:
Bactopeptone: 1.7%
Proteose peptone: 0.3%
D-xylose: 1.0%
NaCl: 0.5%
Bacto Neutral Red: 0.003%
Agar: 1.5%
Distilled $H_2O$: q/s The initial streak was made at the 0% end of the gradient. The streaking continued toward the 3% end as the growing colonies appeared. Finally, resistant colonies from the 3% end of the plate were picked up and screened in flask fermentations for glucose isomerase activity. The fermentation medium consisted of:
Ardamine PH yeast extract: 2.15%
Corn steep liquor: 2.94%
$K_2HPO_4$: 0.8%
$MgSO_4.7H_2O$: 0.02%
NaCl: 0.2%
Distilled $H_2O$: q/s
with 1% of either xylose or glucose as the carbon source.

Several classes of 2-deoxyglucose resistant mutants were obtained in the above manner and their glucose isomerase activity measured by the method of Kennedy and Chaplin (described in Carbohydrate Research, 40, 227–233, 1975), in which glucose is converted to fructose and one unit of enzyme is equivalent to 1 μmole of fructose formed per minute at 70° C. The results are set out in Table I.

TABLE I

| Strain | Resistance to 2-Deoxy Glucose | Glucose Isomerase Activity (units/ml) in Fermentation Medium Containing: | |
|---|---|---|---|
| | | 1% xylose | 1% glucose |
| ATCC 31604 | — | 5.6 | 2.5 |
| DG2 | + | 6.1 | 3.5 |
| ATCC 31667 | + | 3.4 | 6.1 |
| UDG7 | + | 1.0 | 1.0 |

Mutant ATCC 31667 is clearly superior for the production of glucose isomerase in a fermentation broth devoid of xylose.

EXAMPLE II

A culture of mutant ATCC 31667 was grown in a seed medium containing 1% Ardamine pH yeast extract, 0.5% NaCl and 1% D-xylose to a Klett density of about 100 (green filter). This culture was then used to inoculate the fermentation medium (1 part seed: 100 parts fermentation medium) of the following composition:

| | % (w/v) |
|---|---|
| Ardamine PH yeast extract | 2.21 |
| Corn steep liquor | 3.18 |
| $K_2HPO_4$ | 0.80 |
| $KHPO_4$ | 0.20 |
| $MgSO_4.7H_2O$ | 0.02 |
| Distilled $H_2O$ | q/s |

The pH of the medium was adjusted to 7.5 with 50% NaOH whereupon Buffalo Pearl Starch (unhydrolyzed) was added to a concentration of 0.6 g./100 ml. The mixture was autoclaved (15 psi, 121° C., 20 minutes) and glucose added to 1.25 % (w/v) concentration before inoculation.

The fermentations were carried out at 50° C. with the level of dissolved oxygen being either at or near zero or greater than or equal to 20%. The results of this experiment are set out in Table II.

TABLE II

ATCC 31667 FERMENTATION IN 10 LITER VESSELS WITH OR WITHOUT OXYGEN LIMITATION

| Dissolved Oxygen at or near Zero | | Dissolved Oxygen at or above 20% | |
|---|---|---|---|
| Time (hrs.) | Glucose Isomerase (units/ml.) | Time (hrs.) | Glucose Isomerase (units/ml.) |
| 7.5 | 2.0 | 6.25 | 0.8 |
| 8 | 2.0 | 7 | 2.2 |
| 8.5 | 2.7 | 8 | 3.5 |
| 9 | 4.0 | 9 | 5.5 |
| 10 | 6.0 | 10 | 6.5 |
| 11 | 7.7 | 11 | 7.2 |
| 12 | 8.7 | 12 | 7.5 |
| 13 | 9.7 | 13 | 9.2 |
| 14 | 9.7 | 14 | 8.2 |
| 15 | 9.7 | 15 | 9.5 |
| 16 | 8.7 | 16 | 8.2 |
| 17 | 10.0 | 17 | 10.5 |

EXAMPLE III

A stock culture of *Bacillus coagulans* NRRL 5656 was grown in a liquid medium consisting of:

Ardamine PH yeast extract: 1.0%
Bacto-Tryptone: 1.7%
Bacto-Soytone: 0.3%
$K_2HPO_4$: 0.25%
NaCl: 0.5%
D-xylose: 1.0%
Distilled $H_2O$: q/s at 50° C. and at an initial pH of 7.15. The cells were grown to a Klett density of about 60 (green filter), centrifuged and resuspended in 0.1 M $MgSO_4$ so that the optical density at 540 nm was 0.150 as determined with a Bausch & Lomb Spectronic 20 spectrophotometer. A loopful of this suspension was streaked on a solid medium containing a gradient of 2-deoxy-D-glucose concentration from 0 to 3%. The composition of the solid medium was:

Ardamine PH yeast extract: 1.0%
Bacto-Tryptone: 1.7%
Bacto-Soytone: 0.3%
D-xylose: 1.0%
NaCl: 0.5%
$K_2HPO_4$: 0.25%
Agar: 1.5%
Distilled $H_2O$: q/s As in Example I, the initial streak was made at the 0% end of the gradient. The streaking continued toward the 3% end as the growing colonies appeared. Finally, resistant colonies from the 3% end of the plate were picked up and screened in flask fermentations for glucose isomerase activity. The fermentation medium consisted of:

Difco yeast extract: 0.5%
Corn steep liquor: 8.0%
$(NH_4)_2SO_4$: 0.5%
$K_2HPO_4$: 0.1%
$MgSO_4.7H_2O$: 0.02%
$MnSO_4.H_2O$: 0.005%
Distilled $H_2O$: q/s with 0.4% of either xylose or glucose as the carbon source.

Several classes of 2-deoxyglucose resistant mutants were obtained in the above manner and their glucose isomerase activity determined as in Example I. The results of this experiment are set out in Table III.

TABLE III

| Strain | Resistance to 2-Deoxy Glucose | Glucose Isomerase Activity (units/ml) in Fermentation Medium Containing: | |
|---|---|---|---|
| | | 0.4% xylose | 0.4% glucose |
| NRRL 5656 | — | 2.0 | 1.2 |
| Mutant 1 | + | 2.2 | 0.8 |
| Mutant 2 | + | 1.9 | 0.0 |
| Mutant 5 | + | 3.6 | 4.0 |

What is claimed is:

1. A biologically pure culture of an asporogenic bacterium from the genus and species *Bacillus licheniformis* ATCC 31667 which is further identified by being resistant to 2-deoxyglucose, is capable of producing glucose isomerase in greater quantities in a fermentation medium containing appropriate nutrients which medium is devoid of xylose than in a medium with xylose present and whose nutritional demands include the requirement of methionine and the vitamins niacin, riboflavin and thiamine for growth.

2. A method for the production of a glucose isomerase which comprises cultivating *Bacillus licheniformis* ATCC 31667 in an aqueous nutrient medium containing appropriate nutrients for a time sufficient to produce a recoverable quantity of the enzyme.

3. The method of claim 2 wherein the bacterium is cultivated aerobically.

4. A method for screening a mutant strain of a microorganism from the genus Bacillus for the ability to produce glucose isomerase in a medium devoid of xylose which comprises the steps of:
   (a) placing a culture of a nonpathogenic bacterium from the genus Bacillus on a growth support medium;
   (b) allowing the culture to grow and isolating a single colony to obtain a pure clone;
   (c) streaking a single colony of the pure clone on a growth support medium containing 2-deoxyglucose;
   (d) recovering one or more 2-deoxyglucose resistant variants from the growth support medium used in step (c);
   (e) purifying the 2-deoxyglucose resistant variant obtained in step (d) by restreaking it on a growth support medium containing 2-deoxyglucose to thereby eliminate nonresistant dormant cells;
   (f) recovering the purified variant from the growth support medium used in step (e); and
   (g) determining the ability of the purified variant to produce glucose isomerase in a growth support medium devoid of xylose.

5. The method of claim 4 wherein the microorganism is selected from the group of *B. licheniformis, B. coagulans, B. subtilis, B. pumilus* and *B. cereus*.

6. The method of claim 5 wherein the microorganism is *B. coagulans*.

7. The method of claim 5 wherein the microorganism is *B. licheniformis*.

* * * * *